(12) United States Patent
Belledent

(10) Patent No.: US 10,255,298 B2
(45) Date of Patent: Apr. 9, 2019

(54) METHOD FOR DEFINING A SELF-ASSEMBLING UNIT OF A BLOCK COPOLYMER

(71) Applicant: COMMISSARIAT A L'ENERGIE ATOMIQUE ET AUX ENERGIES ALTERNATIVES, Paris (FR)

(72) Inventor: Jérôme Belledent, Meylan (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 250 days.

(21) Appl. No.: 15/114,514

(22) PCT Filed: Feb. 10, 2015

(86) PCT No.: PCT/EP2015/052798
§ 371 (c)(1),
(2) Date: Jul. 27, 2016

(87) PCT Pub. No.: WO2015/121269
PCT Pub. Date: Aug. 20, 2015

(65) Prior Publication Data
US 2016/0342592 A1    Nov. 24, 2016

(30) Foreign Application Priority Data
Feb. 12, 2014 (FR) ..................... 14 51085

(51) Int. Cl.
*G06K 9/00* (2006.01)
*G06F 17/30* (2006.01)
(Continued)

(52) U.S. Cl.
CPC ........ *G06F 17/3028* (2013.01); *G06F 17/141* (2013.01); *G06F 19/707* (2013.01);
(Continued)

(58) Field of Classification Search
CPC .. G06F 17/3028; G06F 17/141; G06F 19/707; G06T 7/001; G06K 9/6202; G06K 9/00147
See application file for complete search history.

(56) References Cited

U.S. PATENT DOCUMENTS

| | | | |
|---|---|---|---|
| 2002/0064909 A1* | 5/2002 | Gracias | B82Y 10/00 438/129 |
| 2010/0323096 A1* | 12/2010 | Sills | B81C 1/00031 427/58 |

(Continued)

OTHER PUBLICATIONS

Christopher Forrey et al., "Molecular Dynamics Study of the Role of the Free Surface on Block Copolymer Thin Film Morphology and Alignment," American Cancer Society Nano, vol. 5, No. 4, 2011, pp. 2895-2907.

(Continued)

*Primary Examiner* — Amir Alavi
(74) *Attorney, Agent, or Firm* — Baker & Hostetler LLP

(57) ABSTRACT

A method for determining a self-assembly pattern of a block copolymer confined inside a closed outline called the guiding outline, comprises the following steps, which are implemented by computer: a) choosing in a database a closed outline called the reference outline that is similar to the guiding outline, a self-assembly pattern of the block copolymer, called the reference pattern, being associated with the reference outline; b) applying a geometric transformation to a plurality of points of said reference pattern in order to convert them to respective points called image points of the self-assembly pattern to be determined. A computer program product for implementing such a method is provided.

20 Claims, 2 Drawing Sheets

(51) Int. Cl.
*G06F 19/00* (2018.01)
*G06K 9/48* (2006.01)
*G06F 17/14* (2006.01)
*G06K 9/62* (2006.01)
*G06T 7/00* (2017.01)

(52) U.S. Cl.
CPC ............ *G06K 9/00147* (2013.01); *G06K 9/48* (2013.01); *G06K 9/6202* (2013.01); *G06T 7/001* (2013.01)

(56) References Cited

U.S. PATENT DOCUMENTS

| | | | | |
|---|---|---|---|---|
| 2012/0164389 | A1* | 6/2012 | Yang | B82Y 10/00 428/172 |
| 2014/0069325 | A1* | 3/2014 | Kawanishi | C30B 19/00 117/54 |
| 2014/0141211 | A1* | 5/2014 | Han | C23C 18/1635 428/201 |
| 2014/0357083 | A1* | 12/2014 | Ling | H01L 21/31138 438/694 |
| 2014/0363072 | A1* | 12/2014 | Van Heesch | G06F 17/5045 382/141 |
| 2016/0342592 | A1* | 11/2016 | Belledent | G06F 19/707 |
| 2018/0033638 | A1* | 2/2018 | Ku | H01L 21/31133 |

OTHER PUBLICATIONS

T. Nakano et al., "Dissipative particle dynamics study on directed self-assembly in holes," Proc. of SPIE 8680, Alternative Lithographic Technologies V, 86801I, Mar. 26, 2013.

He Yi et al., "Computational simulation of block copolymer directed self-assembly in small topographical guiding templates," Proc. SPIE 8680, Alternative Lithographic Technologies V, 86801L, Mar. 26, 2013.

Kenji Yoshimoto et al., "Large-scale dynamics of directed self-assembly defects on chemically pre-patterned surface," Proc. SPIE 8680, Alternative Lithographic Technologies V, 86801I, Mar. 26, 2013.

Q. Chen et al., "Directed self-assembly of a colloidal kagome lattice," Nature, vol. 469, No. 7330, Jan. 19, 2011, pp. 381-384, XP055156645.

M. Muller et al., "Computational Approaches for the Dynamics of Structure Formation in Self-Assembling Polymeric Materials," Annual Review of Materials Research, vol. 43, No. 1, May 1, 2013, pp. 1-34, XP055152976.

H-Ch. Kim et al., "Block copolymer based nanostructures: materials, processes, and applications to electronics," Chemical Reviews, vol. 110, No. 1, Dec. 1, 2009, pp. 146-177, XP055156903.

S-J. Jeong et al., "Directed self-assembly of block copolymers for next generation nanolithography," Materials Today, vol. 16, No. 12, Dec. 1, 2013, pp. 468-476, XP055152922.

* cited by examiner

METHOD FOR DEFINING A SELF-ASSEMBLING UNIT OF A BLOCK COPOLYMER

CROSS-REFERENCE TO RELATED APPLICATIONS

This application is a National Stage of International patent application PCT/EP2015/052798, filed on Feb. 10, 2015, which claims priority to foreign French patent application No. FR 1451085, filed on Feb. 12, 2014, the disclosures of which are incorporated by reference in their entirety.

FIELD OF THE INVENTION

The invention relates to a computer-implemented method for determining a self-assembly pattern of a block copolymer confined inside a closed outline.

BACKGROUND

Directed self-assembly (DSA) of block copolymers is drawing an increasing amount of attention as a technology allowing surface patterns to be produced at the nanoscale, thereby surmounting lithography resolution limits. In particular, this technology seems to be well suited to the production of patterns of lines (conductive tracks) and holes (VIAs) in next-generation integrated circuits.

The separation of the phases of block copolymers (BCPs) forms, by self-assembly, nanodomains in the shape of cylinders, spheres or lamellae the spatial scale of which varies from a few nanometers to a few tens of nanometers. Among these various structures, cylindrical domains turn out to be particularly suitable for producing interconnect holes in integrated circuits. In an approach known as graphoepitaxy, the self-assembly of a BCP occurs inside a guiding outline or template produced beforehand on a surface. The high lateral confinement induced by the walls of this guiding outline predictably modifies the "natural" free-surface arrangement of the nanodomains (a hexagonal pattern in the case of cylindrical domains perpendicular to the substrate). Thus, it has been proved that the use of a suitable guiding outline allows an arbitrary arrangement of nano-cylinders to be formed, which may correspond to a pattern of interconnect holes in an integrated circuit.

The guiding outlines for graphoepitaxy are typically produced by lithography, and have a shape that inevitably differs from that desired and defined by the lithography mask. It is therefore necessary to check whether the directed self-assembly pattern that will be obtained from a "real" guiding outline—viewed for example by scanning electron microscope—will be sufficiently close to the expected pattern, depending on the targeted application. To do this, it is possible to use numerical simulations based on physical models of the self-assembly process. These physical models may be separated into two broad families: particle-based models and those based on energy fields. By way of non-limiting example, the following publications may be cited:

As regards particle-based models:
"Dissipative particle dynamics study on directed self-assembly in holes" T. Nakano; M. Matsukuma; K. Matsuzaki; M. Muramatsu; T. Tomita; T. Kitano Proc. SPIE 8680, Alternative Lithographic Technologies V, 86801J (Mar. 26, 2013)
"Molecular Dynamics Study of the Role of the Free Surface on Block Copolymer Thin Film Morphology and Alignment Christopher Forrey", Kevin G. Yager, and Samuel P. Broadaway ACS Nano, 2011, 5 (4), pp 2895-2907

As regards models based on energy fields:
"Computational simulation of block copolymer directed self-assembly in small topographical guiding templates" He Yi; Azat Latypov; H.-S. Philip Wong Proc. SPIE 8680, Alternative Lithographic Technologies V, 86801 L (Mar. 26, 2013)
"Large-scale dynamics of directed self-assembly defects on chemically pre-patterned surface" Kenji Yoshimoto; Takashi Taniguchi Proc. SPIE 8680, Alternative Lithographic Technologies V, 86801I (Mar. 26, 2013);

All these methods implement iterative algorithms; they are therefore much too slow to be used in the production phase.

SUMMARY OF THE INVENTION

The invention aims to remedy this drawback of the prior art by providing a method for determining a self-assembly pattern of a block copolymer confined inside a closed outline, which is faster than known methods while still being sufficiently precise and predictive. More particularly, the invention aims to provide a method that is fast enough to be used to determine such self-assembly patterns over the entire area of an integrated circuit.

According to the invention, this aim is achieved using a method based on a simple geometric transformation of a "reference" outline, which is indexed in a database stored in the memory of a computer and identified as being the closest to the guiding profile in question.

Thus, one subject of the invention allowing this aim to be achieved is a method for determining a self-assembly pattern of a block copolymer confined inside a closed outline called the guiding outline, including the following steps, which are implemented by computer:

a) choosing in a database a closed outline called the reference outline that is similar to said guiding outline, a self-assembly pattern of said block copolymer, which is called the reference pattern, being associated with said reference outline;

b) applying a geometric transformation to a plurality of points of said reference pattern in order to convert them to respective points called image points of the self-assembly pattern to be determined, said geometric transformation being a function of a geometric transformation allowing said reference outline to be converted to said guiding outline.

According to various particular embodiments of such a method:

Said reference pattern may comprise at least one first phase and one second phase, said points of said reference pattern being chosen so as to sample a boundary between said first phase and said second phase.

Said database may contain a plurality of closed outlines sampled according to a sampling method; the method comprising a prior step of sampling said guiding outline according to the same sampling method and with the same number of sampling points as at least some of the closed outlines contained in said database.

The curvilinear distance between two said sampling points may be, for all the closed outlines contained in said database and for said guiding outline, comprised between half and twice a predefined length s0.

Said predefined length $s_0$ may be such that $L_0/5 \leq s_0 \leq 5L_0$, preferably $L_0/2 \leq s_0 \leq 2L_0$ and even more preferably $L_0/2 \leq s_0 \leq L_0$, where $L_0$ is a natural period of said block copolymer.

Said step a) may comprise:
  a1) selecting closed outlines from said database including as many sampling points as said guiding outline; and
  a2) choosing, from the closed outlines thus selected, that which minimizes a distance criterion dependent on the coordinates of the sampling points of said closed outline and of said guiding outline.

Said distance criterion may be a quadratic distance between the complex coefficients obtained by discrete Fourier transform of two vectors of complex numbers representing the coordinates of the sampling points of said closed outline and of said guiding outline, respectively.

Said database may contain, for each said closed outline, a dataset defining a triangulation of an area bounded by said outline, and said step b) may comprise:
  b1) determining a triangulation of an area bounded by said guiding outline, each triangle and each apex of said triangulation being associated with a respective triangle and a respective apex of said triangulation of the area bounded by the reference outline; and
  b2) for a plurality of points of said reference pattern, each of which is contained in a triangle of said triangulation of the area bounded by the reference outline, determining an image point contained in the associated triangle of said triangulation of the area bounded by said guiding outline.

Each said point of said reference pattern and its image point may have, with respect to the triangles in which they are respectively contained, the same barycentric coordinates.

Said step b2) may also comprise:
  b2') for each or at least one of said points of said reference pattern, constructing at least one additional triangle containing said point and the apexes of which are located on said reference outline;
  the image point of said or each said point of the reference pattern having, with respect to the triangle in which it is contained, barycentric coordinates obtained by linear combination of the barycentric coordinates of said point of the reference pattern with respect to the triangles in which it is contained.

The triangulation of said outlines may be performed while taking, by way of apexes, at least some of said sampling points.

Such a method may also include the following step:
  c) using a self-assembly model of said block copolymer (in other words, a physical modelling algorithm) to determine said self-assembly pattern, while using said image points by way of initialization data.

Another subject of the invention is a computer program product comprising programming code instructions for executing steps of such a method when said program is executed on a computer.

BRIEF DESCRIPTION OF THE DRAWINGS

Other features, details and advantages of the invention will become apparent on reading the description, which is given with reference to the appended drawings, which are given by way of example, in which drawings.

DETAILED DESCRIPTION

The invention will be described using examples in which the block copolymer considered is of the cylindrical (i.e. forming nanocylinders by self-assembly) PS-b-PMMA type. However, the invention may be applied to other types of block copolymers (di-block copolymers, star-shaped or linearly structured tri-block copolymers, etc.) and to blends of such copolymers. Furthermore, there are no restrictions on the type of graphoepitaxy method used (solvent annealing, layer grafting, etc.).

Figure 1A:
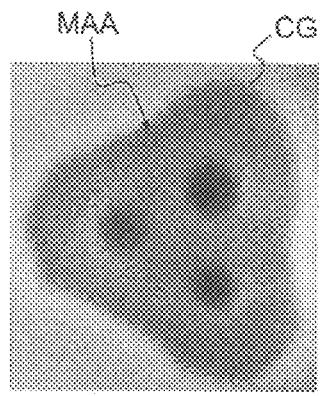
FIG. 1A is a scanning electron micrograph of a guiding outline and of the associated self-assembly pattern.
Figure 1B:
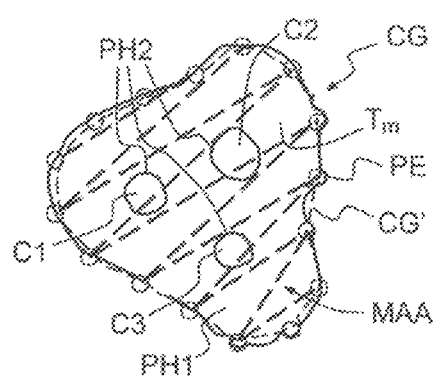
FIG. 1B shows the same outline sampled with its triangulation.

FIG. 1A illustrates a scanning electron micrograph of a self-assembly pattern MAA of a block copolymer (PS-b-PMMA) confined by a closed guiding outline CG of trilobed shape. This pattern comprises a continuous first phase (referenced PH1 in FIG. 1B) and a discrete second phase (referenced PH2 in FIG. 1B) formed by three cylinders (C1, C2 and C3 in FIG. 1B). The image is digitized and acquired by a computer. Next, as shown in FIG. 1B, the outline CG is sampled. In the present case, the sampling is regular, i.e. with sampling points PE arranged substantially equidistantly from one another along the outline. For reasons of computational efficiency which will be explained below, it is preferable for the number of sampling points to be a power of 2—here $16=2^4$. The points are ordered and arranged on the outline in the anticlockwise direction. The reference CG' corresponds to a polygon the apexes of which coincide with the sampling points and which is similar to the guiding outline (discretized outline). The boundaries of the cylindrical domains C1, C2 and C3 are also sampled, although this is not shown in the figure.

Next, a triangulation of the area bounded by the outline CG (or, more exactly, by the discretized outline CG') is defined by taking the sampling points E as apexes of the triangles. The reference $T_m$ in FIG. 1B identifies one of these triangles.

A plurality of discretized images of the type in FIG. 1B, corresponding to different outlines for guiding the self-assembly of a given block copolymer, are stored in the memory of the computer in order to form a database or library. These images may correspond to real samples, or be obtained from high-precision physical models. FIGS. 2A to 2G show the images of such a database.

In the database, each image may be represented by:

The coordinates of the sampling points PE of the guiding outline; in particular, each sampling point may be represented by a complex number $z=x+jy$, where "j" is the imaginary unit and (x, y) the Cartesian coordinates of the sampling point.

Data identifying the triangulation; for example, each triangle may be identified by three integers identifying the sampling points serving it as apexes.

The coordinates of the sampling points P (see FIG. 2A) of the boundaries of the cylindrical domains (more generally, of the boundaries between different phases of the self-assembly pattern). More particularly, each of these points may be identified by its barycentric coordinates in the triangle containing it, and by an identifier of this triangle. As will be explained below, with reference to FIG. 3, a given point P may be located inside a plurality of triangles, in which case a plurality of sets of barycentric coordinates may be stored in the database. It will be recalled that the barycentric coordinates of a point with respect to a triangle are the masses that must be given to the apexes of said triangle for said point to be the geometric centroid thereof (the masses possibly being negative, if the point in question is located outside the triangle).

The Fourier transform of the sampled outline may also be stored in the database, thereby avoiding the need to have to calculate it subsequently. As explained above, each sampling point may be identified by a complex number; thus, the discretized outline CG' is represented by a complex vector, the Fourier transform of which may be calculated. The reason why a number of sampling points equal to a power of two is preferably chosen is that this allows a fast Fourier transform (FFT) algorithm to be used.

Advantageously, the curvilinear distance between two sampling points is approximately the same for all the images in the database, and more precisely is comprised between half and twice a reference length $s_0$. More particularly, it is possible to require that the distance "s" between an arbitrary pair of adjacent sampling points satisfy the inequality $|s-s_0| \leq 0.4 \cdot s_0$. The reference length is preferably of the same order of magnitude as the natural period $L_0$ of the copolymer, i.e. the distance between domains (for example cylindrical domains) in case of free, i.e. unconstrained by a guiding outline, self-assembly of the copolymer. For example, it is possible for $L_0/5 \leq s_0 \leq 5L_0$, more particularly for $L_0/2 \leq s_0 \leq 2L_0$ and even more particularly for $L_0/2 \leq s_0 \leq L_0$, and, by way of particular example, for $s_0 = L_0$.

The number of sampling points on an outline of length L may then be given by:

$$N = 2^{E\left[0.5 + \frac{\log\left(\frac{L}{s_0}\right)}{\log(2)}\right]}$$

where "E" is the "floor" function.

To implement a method according to the invention, it is preferable, for reasons that will become apparent below, for the numbering of the sampling points not to be arbitrary.

To do this, a particular guiding outline is centered beforehand so its center of gravity "g" is placed at the origin of a Cartesian coordinate system. Next, the outline is sampled in the anticlockwise direction. As was explained above, the resulting set of sampling points then consists of complex numbers $(c_i)_{1 \leq i \leq N}$ such that the curvilinear distance separating them is equal to $$s = \frac{L}{N}$$

and such that the x-axis and the vector $\overrightarrow{gc_1}$ make between them an angle equal to $$\theta_0 = \frac{(\text{Arg}(\tilde{c}_2) + \text{Arg}(\tilde{c}_N))}{2},$$

where $(\tilde{c}_i)_{1 \leq i \leq N}$ are the values of the discrete Fourier transform of $(c_i)_{1 \leq i \leq N}$ and "Arg" is the function giving the argument of a complex number. It should be noted that $\theta_0$ is the orientation of the major axis of an ellipse approximating the outline.

The triangulation of the area bounded by the guiding outline thus sampled may then be performed in the following way:

The first triangle $T_1$ has for apexes the points $p_1 = c_1$, $q_1 = c_2$ and $r_1 = c_N$.

The triangles $$(T_{2i})_{1 \leq i \leq \frac{N}{2} - 2}$$

have for apexes the points $p_{2i} = c_{i+1}$, $q_{2i} = c_{i+2}$ and $r_{2i} = c_{N-i+1}$ The triangles $$(T_{2i+1})_{1 \leq i \leq \frac{N}{2} - 2}$$

have for apexes the points $p_{2i+1} = c_{i+2}$, $q_{2i+1} = c_{N-i}$ and $r_{2i+1} = c_{N-i+1}$.

It may be of interest to note that this triangulation is not, in general, a Delaunay triangulation unless the polygon CG' is convex. If the triangulation is not a Delaunay triangulation, the triangles will possibly superpose, and therefore a particular point of the pattern MAA will possibly be contained in a plurality of triangles. This does not affect the implementation of the method of the invention.

Once the database has been formed, the problem to be solved is that of determining the self-assembly pattern of a given copolymer inside a guiding outline other than those contained in the database. To do this, this outline (without the copolymer inside) must be sampled as explained above; the number N of sampling points on the outline must be the same as for at least one portion of the database. A triangulation of the area bounded by this outline must furthermore be determined in the same way used during construction of said database.

Next, it is necessary to determine, among those outlines stored in the database which have N sampling points, that which is the most similar to the guiding outline for which it is desired to determine the self-assembly pattern; the outline thus determined will be called the "reference outline" below. To do this, it is necessary to define a criterion of similarity of the outlines. Advantageously, but nonlimitingly, it will possibly be a question of the quadratic distance between the Fourier coefficients of the outlines:

$$\sum_{i=1}^{N} \left(|\tilde{c}'_i|^2 - |\tilde{c}_i|^2\right)$$

where $\tilde{c}_i$ is the ith Fourier coefficient of the guiding outline to be characterized and $\tilde{c}'_i$ that of the outline of the database to which said guiding outline is being compared. The discrete Fourier transform of an outline is calculated as was explained above, each sampling point being represented by a complex number. The numbering of the sampling points must follow a convention common to all the outlines (for example, but nonlimitingly, that explained above) in order for the quadratic distance thus calculated to have meaning. It should be noted that information on the rotation of the outline and on the origin of the sampling is contained in the phase of the Fourier spectrum. Desirably, they are therefore not taken into account during the comparison of the outlines.

In other words, a double filter is applied to the database: first the outlines that have a length close to that of the outline to be characterized are pre-selected (by counting the number of sampling points), then a single reference outline is selected by applying a suitable similarity criterion.

Once the reference outline has been found in the library, the guide to be characterized is rotated so as to minimize the distance between the two sets of sampling points. This position may be obtained with a good approximation by applying a rotation of angle equal to that made by the vectors $\overrightarrow{gc_1}$ and $\overrightarrow{g'c'_1}$, g' being the center of gravity of the reference outline.

At this stage, a geometric transformation may be applied that converts the self-assembly pattern associated with the reference outline ("reference pattern")—which is known and stored in the database—to a pattern similar to that which will be obtained when the given block copolymer self assembles inside the guiding outline to be characterized.

This geometric transformation is based on the triangulations, and more precisely on the fact that each sampling point of the outline to be characterized is associated with ("is the image of") a respective sampling point of the reference outline, and that each triangle of the triangulation of the area bounded by the outline to be characterized is associated with a respective triangle of the triangulation of the area bounded by the reference outline. Thus, it is possible to identify a plurality of points of the reference pattern, to determine the triangle in which each of these points is contained and to associate therewith an image point contained in the associated triangle of the triangulation of the area bounded by the outline to be characterized. More particularly, a point of the reference pattern may be characterized by its barycentric coordinates ($\alpha$, $\beta$, $\gamma$) with respect to the triangle containing it, and its image point by identical barycentric coordinates ($\alpha_{IM}$, $\beta_{IM}$, $\gamma_{IM}$)=($\alpha$, $\beta$, $\gamma$) with respect to the triangle associated therewith.

It is not particularly difficult to determine in which triangle a given point of the reference pattern is located. For example, all the triangles may be considered in sequence the barycentric coordinates of the point with respect to each of said triangles being calculated and the process stopped when $\alpha+\beta+\gamma=1$ where $\alpha$, $\beta$ and $\gamma$ are comprised between 0 and 1. At this stage it is possible to store this information in the database.

Figure 2A:
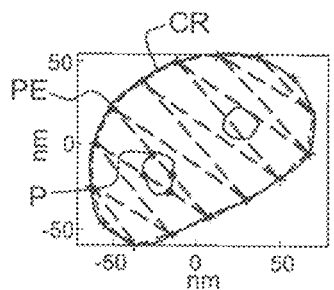
FIGS. 2A-2G show respective reference profiles able to be stored in a database.
Figure 2B:
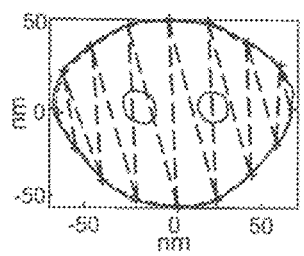
Figure 2C:
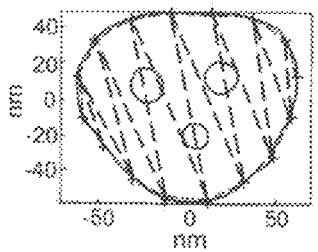
Figure 2D:
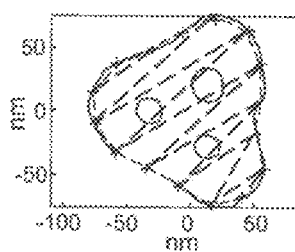
Figure 2E:
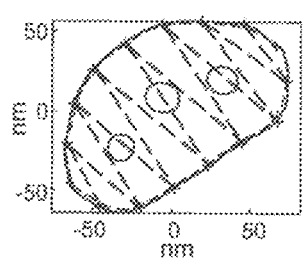
Figure 2F:
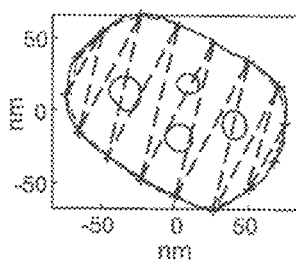
Figure 2G:
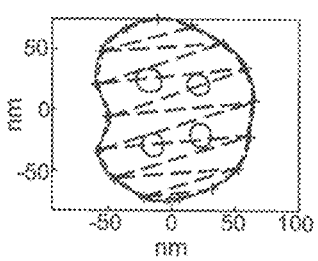

For the sake of efficiency, this geometric transformation will advantageously only be applied to sampling points on the boundary of the cylindrical domains (more generally: the boundary between phases) in the reference pattern (point "P" in FIG. 2A). Specifically, knowledge of these points is enough to reconstruct a self-assembly pattern to a good approximation.

A difficulty arises from the fact that the characteristic length scale of the triangulation on which the geometric transformation is based is generally smaller than the length of the walls of the guiding outline, this influencing the positions of the cylindrical domains formed by self-assembly of the copolymer. The present inventor has therefore concluded that it would be advantageous to also use additional triangles with larger base lengths (not having two apexes consisting of adjacent sampling points) in the geometric transformation. In particular, it has been found that a number of triangles nbTri=3 is generally satisfactory.

The additional triangles associated with the triangle $T_m$ of the triangulation may be even in number and be defined as follows:

If m=2i+1 is uneven ("i" being an integer):
The additional triangle $T_{m,2k}$ has for apexes the points $p_{m,2k}=c_{i+2-k}$, $q_{m,2k}=c_{i+2+k}$ and $r_{m,2k}=c_{N-i}$; and the additional triangle $T_{m,2k+1}$ has for apexes the points $p_{m,2k+1}=c_{i+2}$, $q_{m,2k}=c_{N-i-k}$ and $r_{m,2k}=c_{N-i+1+k}$.

If m=2i is even:
The additional triangle $T_{m,2k}$ has for apexes the points $p_{m,2k}=c_{i+1-k}$, $q_{m,2k}=c_{i+2+k}$ and $r_{m,2k}=c_{N-i+1}$; and the additional triangle $T_{m,2k+1}$ has for apexes the points $p_{m,2k+1}=c_{i+1}$, $q_{m,2k}=c_{N-i+1-k}$ and $r_{m,2k}=c_{N-i+1+k}$.

Where k is comprised between 1 and (nbTri−1)/2. In the above formulae, it is possible for the indices of the points c not to be comprised between 1 and N. In this case, the triangle cannot be constructed and a restricted set of barycentric coordinates will be used.

Figure 3:
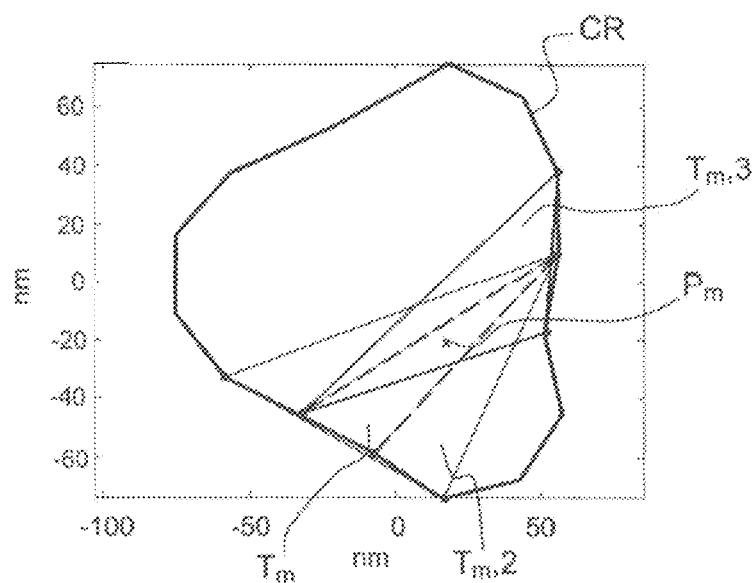
FIG. 3 illustrates the use of additional triangles in a method according to one particular embodiment of the invention.

FIG. 3 shows a point $P_m$ located inside a triangle $T_m$ forming part of the triangulation of the reference outline CR, and two additional triangles $T_{m,2}$ and $T_{m,3}$. In this case, nbTri=3.

If additional triangles are used, the geometric transformation must be redefined. If a point P of the reference pattern MR contained in nbTri triangles (one triangle $T_m$ belonging to the triangulation and nbTri−1 additional triangles) is considered, the image point will be located in the triangle of the triangulation of the outline to be characterized associated with $T_m$, and its barycentric coordinates with respect to this triangle will be given by a weighted mean of its barycentric coordinates in the various triangles of the reference outline. The weighting coefficients will typically be chosen such that the image of a point located on the reference outline is located on the outline to be characterized.

A given point P of the guide located in the triangle $T_{m,1}$ has for image the point PIM such that:

$$P_{PIM} = \frac{\sum_{k=1}^{nbTri} \prod_{l \neq k} \alpha_l \beta_l \gamma_l (\alpha_k p_k + \beta_k q_k + \gamma_k r_k)}{\sum_{k=1}^{nbTri} \prod_{l \neq k} \alpha_l \beta_l \gamma_l}$$

where:
$P_{PIM}$ is the complex number representing the Cartesian coordinates of the image point PIM;
The index "k" identifies the nbTri triangles $T_k$ containing the point P—typically one triangle belonging to the triangulation of the area bounded by the reference outline and (nbTri−1) additional triangles;
$p_k$, $q_k$ and $r_k$ are the complex numbers representing the Cartesian coordinates of the apexes of the triangle $T_k$; and
$\alpha_k$, $\beta_k$, $\gamma_k$ and $\alpha_l$, $\beta_l$, $\gamma_l$ are respectively the barycentric coordinates of the point P in the triangles $T_k$ and $T_l$.

In the case where nbTri=1 (meaning that there are no additional triangles) the above equation simplifies to the following:

$P_{PIM}=\alpha p+\beta q+\gamma r$

Figure 4:
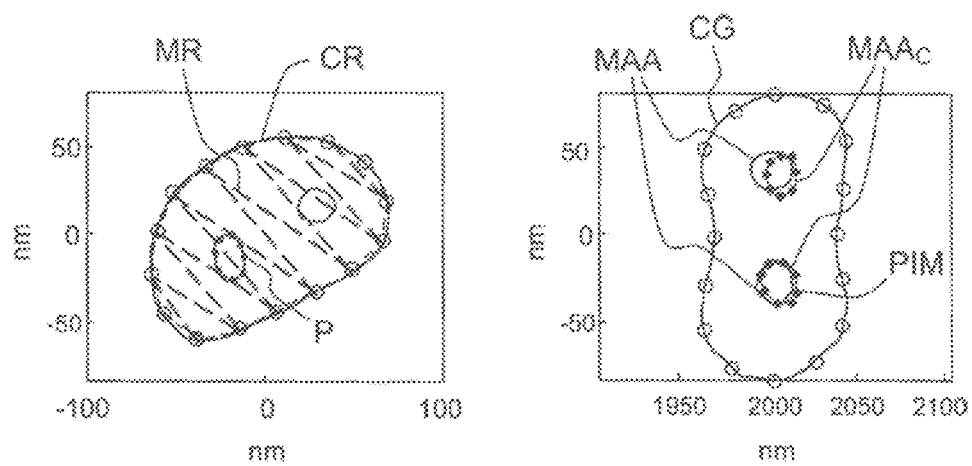
FIG. 4 illustrates the technical result of the invention.

The right- and left-hand portions of FIG. 4 respectively show a guiding outline CG to be characterized and the corresponding reference outline CR with the associated reference pattern MR. The boundaries of the two cylindrical domains contained in this reference pattern MR are sampled; one of the sampling points has been identified by the reference P. A geometric transformation such as described above, with nbTri=3, was applied to find the image points of the sampling points inside the outline CG to be characterized; for example, the reference PIM identifies the image point of the aforementioned point P. In the right-hand portion of the figure, the reference MAAc identifies the calculated self-assembly pattern formed by all the image points of the sampling points of the boundaries of the cylindrical domains of the reference pattern. It may be seen that this calculated pattern is very close to the "true" self-assembly pattern MAA, here determined experimentally (but recourse could have also been made to a physical model). Optionally, it is possible to use the calculated self-assembly pattern MAAc to initialize a self-assembly modelling algorithm; in this case, the latter may be expected to converge in only a few iterations. It may for example be a question of a physical modelling algorithm.

A plurality of variants of the method that was just described may be envisioned without departing from the scope of the present invention. For example, similarity criteria other than the quadratic distance between the Fourier coefficients of the outlines may be used. Furthermore, it is possible to envision sampling each outline twice, one sample being intended for the measurement of the similarity of the outlines and the other for the triangulation. As regards the actual sampling, various methods may be used provided that the same method is used for the reference outlines and the outline to be studied. Such a sampling method must in particular allow N points to be identified on the outline and the position of the first point on this outline and a direction of travel around the outline to be set. Moreover, the relationship between a point of the reference pattern and its image point in the calculated self-assembly pattern may not be based on the barycentric coordinates of the points. It may more generally be a question of any relationship given by a geometric transformation that is a function of the geometric transformation allowing the reference outline to be converted to the guiding outline in question.

The invention claimed is:

1. A method for determining a self-assembly pattern of a block copolymer confined inside a closed outline called a guiding outline, including the following steps, which are implemented by computer:
    a) forming a database by acquiring and/or storing in a memory of the computer a plurality of discretized images corresponding to different guiding outlines of the self-assembly pattern of a given block copolymer; and choosing with the computer from the database a closed outline called a reference outline that is similar to said guiding outline, a self-assembly pattern of said block copolymer, which is called a reference pattern, being associated with said reference outline; and
    b) applying with the computer a geometric transformation to a plurality of points of said reference pattern in order to convert the plurality of points to respective points called image points of the self-assembly pattern to be determined, said geometric transformation being a function of a geometric transformation allowing said reference outline to be converted to said guiding outline.

2. The method of claim 1, wherein said reference pattern comprises at least one first phase and one second phase, said plurality of points of said reference pattern being chosen so as to sample a boundary between said first phase and said second phase.

3. The method of claim 1, wherein said database contains a plurality of closed outlines sampled according to a sampling method; the method comprising a prior step of sampling said guiding outline according to the same sampling method and with the same number of sampling points as at least some of the closed outlines contained in said database.

4. The method of claim 3, wherein a curvilinear distance between two said sampling points is, for all the closed outlines contained in said database and for said guiding outline, comprised between half and twice a predefined length $s_0$.

5. The method of claim 4, wherein said predefined length $s_0$ is such that $L_0/5 \leq s_0 \leq 5L_0$, where $L_0$ is a natural period of said block copolymer.

6. The method of claim 4, wherein said predefined length $s_0$ is such that $L_0/2 \leq s_0 \leq 2L_0$, where $L_0$ is a natural period of said block copolymer.

7. The method of claim 4, wherein said predefined length $s_0$ is such that $L_0/2 \leq s_0 \leq L_0$, where $L_0$ is a natural period of said block copolymer.

8. The method of claim 3, wherein said step a) comprises:
    a1) selecting closed outlines from said database including as many sampling points as said guiding outline; and
    a2) choosing, from the closed outlines thus selected, that which minimizes a distance criterion dependent on coordinates of the sampling points of said closed outline and of said guiding outline.

9. The method of claim 8, wherein said distance criterion is a quadratic distance between complex coefficients obtained by discrete Fourier transform of two vectors of complex numbers representing the coordinates of the sampling points of said closed outline and of said guiding outline, respectively.

10. The method of claim 3, wherein said database contains, for each said closed outline, a dataset defining a triangulation of an area bounded by said outline, and wherein said step b) comprises:
    b1) determining a triangulation of an area bounded by said guiding outline, each triangle and each apex of said triangulation being associated with a respective triangle and a respective apex of said triangulation of the area bounded by the reference outline; and
    b2) for a plurality of points of said reference pattern, each of which is contained in a triangle of said triangulation of the area bounded by the reference outline, determining an image point contained in the associated triangle of said triangulation of the area bounded by said guiding outline; and wherein the triangulation of said outlines is performed while taking, by way of apexes, at least some of said sampling points.

11. The method of claim 1, wherein said database contains, for each said closed outline, a dataset defining a triangulation of an area bounded by said outline, and wherein said step b) comprises:
    b1) determining a triangulation of an area bounded by said guiding outline, each triangle and each apex of said triangulation being associated with a respective triangle and a respective apex of said triangulation of the area bounded by the reference outline; and
    b2) for a plurality of points of said reference pattern, each of which is contained in a triangle of said triangulation of the area bounded by the reference outline, determining an image point contained in the associated triangle of said triangulation of the area bounded by said guiding outline.

12. The method of claim 11, wherein each said point of said reference pattern and its image point have, with respect to triangles in which they are respectively contained, the same barycentric coordinates.

13. The method of claim 11, wherein said step b2) also comprises:

b2') for each or at least one of said points of said reference pattern, constructing at least one additional triangle containing said point and the apexes of which are located on said reference outline;

the image point of said or each said point of the reference pattern having, with respect to the triangle in which it is contained, barycentric coordinates obtained by linear combination of the barycentric coordinates of said point of the reference pattern with respect to the triangles in which it is contained.

14. The method of claim 1 also including the following step:

c) using a self-assembly model of said block copolymer to determine said self-assembly pattern, while using said image points by way of initialization data.

15. The method of claim 1, further comprising determining and outputting with the computer a criterion of similarity between the guiding outline and the reference outline.

16. The method of claim 1, further comprising producing at least a portion of a pattern for an integrated circuit having the self-assembly pattern of a block copolymer based on a criterion of similarity between the guiding outline and the reference outline.

17. The method of claim 1, further comprising a step prior to step a) of acquiring a discretized image of the guiding outline.

18. A non-transitory computer program product comprising programming code instructions for executing steps of a method for determining a self-assembly pattern of a block copolymer confined inside a closed outline called a guiding outline when said non-transitory computer program is executed on a computer, the method including the following steps:

a) forming a database by acquiring and/or storing in a memory of the computer a plurality of discretized images corresponding to different guiding outlines of the self-assembly pattern of a given block copolymer; and choosing with the computer from the database a closed outline called a reference outline that is similar to said guiding outline, a self-assembly pattern of said block copolymer, which is called the reference pattern, being associated with said reference outline; and b) applying with the computer a geometric transformation to a plurality of points of said reference pattern in order to convert the plurality of points to respective points called image points of the self-assembly pattern to be determined, said geometric transformation being a function of a geometric transformation allowing said reference outline to be converted to said guiding outline.

19. The non-transitory computer program product of claim 18, further comprising determining and outputting with the computer a criterion of similarity between the guiding outline and the reference outline.

20. The non-transitory computer program product of claim 18, further comprising producing at least a portion of a pattern for an integrated circuit having the self-assembly pattern of a block copolymer based on a criterion of similarity between the guiding outline and the reference outline.

* * * * *